United States Patent [19]

Turner

[11] 4,143,225
[45] Mar. 6, 1979

[54] HOMOPOLYMERS OF A FLUORENONE DERIVATIVE HAVING PENDANT ELECTRON ACCEPTOR GROUPS

[75] Inventor: Sam R. Turner, Webster, N.Y.

[73] Assignee: Xerox Corporation, Stamford, Conn.

[21] Appl. No.: 799,845

[22] Filed: May 23, 1977

Related U.S. Application Data

[62] Division of Ser. No. 596,690, Jul. 16, 1975, Pat. No. 4,062,886.

[51] Int. Cl.$^2$ .................. C08G 65/02; C08G 2/00; C08G 2/16
[52] U.S. Cl. .................. 528/220; 96/1 PE; 96/115 P; 260/30.4 N; 526/218; 526/244; 526/246; 526/273; 526/284; 528/225
[58] Field of Search .............. 260/2 A, 63 UX, 63 K, 260/63 BR, 66, 2 N; 528/220, 225

[56] References Cited

U.S. PATENT DOCUMENTS 4,011,266   3/1977   Pearson et al. .................. 260/63 UX

*Primary Examiner*—Herbert J. Lilling
*Attorney, Agent, or Firm*—J. J. Ralabate; A. A. Mahassel; J. P. O'Sullivan

[57] ABSTRACT

Disclosed are monomers of the formula:

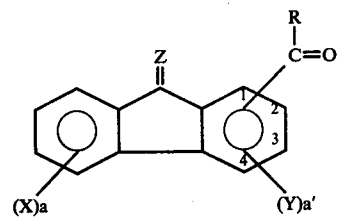

wherein R is

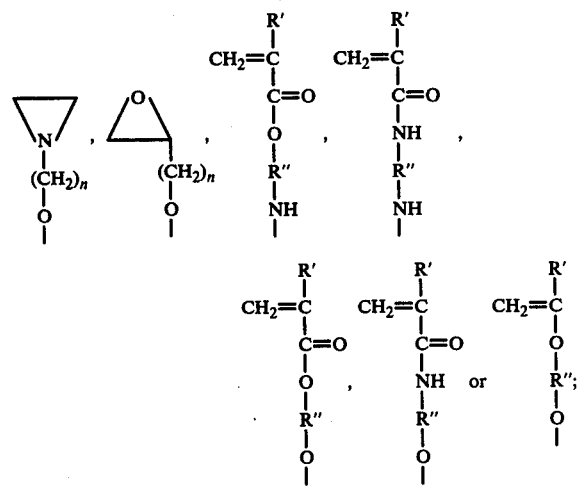

R' is hydrogen or methyl;
R'' is alkyl of 1-10 carbon atoms;
X and Y are independently selected from the group consisting of $NO_2$, halogen, cyano and $-CF_3$;
Z is oxygen or dicyanomethylene;
a and a' can range from 0-3; and
n is 1-10.

These monomers can be readily polymerized to polymers suitable for use in electrophotographic imaging members and methods.

1 Claim, No Drawings

HOMOPOLYMERS OF A FLUORENONE DERIVATIVE HAVING PENDANT ELECTRON ACCEPTOR GROUPS

This is a division of application Ser. No. 596,690, filed July 16, 1975, now U.S. Pat. No. 4,062,886.

BACKGROUND OF THE INVENTION

1. Field of the Invention

This invention relates to a process for preparation of monomers and the polymers derived therefrom. In addition, this invention also embraces the use of such monomers and polymers in electrophotographic imaging members and reproduction systems.

2. Description of the Prior Art

In the electrophotographic arts the photoresponsive component of the imaging member has been traditionally constructed so that one layer of photoconductive material has been primarily responsible for the absorption of imaging energies, the generation of charge carriers in response thereto and the transport of such charge carriers throughout the bulk of the layer. The electronic properties of the materials used in such a layer should be capable of rapid switching from insulating to conductive to insulating state in order to permit cyclic use of the imaging surface of said layer. The failure of a material to return to its relatively insulating state prior to the succeeding charging sequence will result in a decrease in the maximum charge acceptance of the photoconductor. This phenomenon, commonly referred to in the art as "fatigue", has in the past been avoided by the selection of photoconductive materials possessing rapid switching capacity. Typical of the materials suitable for use in such a rapidly cycling imaging system include anthracene, sulfur, selenium and mixtures thereof (U.S. Pat. No. 2,297,691); selenium being preferred because of its superior photosensitivity.

In addition to anthracene, other organic photoconductive materials, most notably poly(N-vinylcarbazole), have been the focus of increasing interest in electrophotography. Most organic photoconductive materials including poly(N-vinylcarbazole) lack the inherent photosensitivity to be competitive with selenium. This need for enhancement of the photoresponse characteristics of organic photoconductors thus lead to the formulation of these organic materials with other compounds, commonly referred to as "activators". Poly(vinylcarbazoles), for example, when sensitized with 2,4,7-trinitro-9-fluorenone exhibit good photoresponse and discharge characteristics and (depending upon the polarity of the surface charge), low dark decay, U.S. Pat. No. 3,484,237. Ordinarily, the bulk absorption of activating electromagnetic radiation and the consequent generation of charge carriers can and often does result in some trapping of at least one species of charge carrier within the photoconductive layer and thus some impairment in the cycling characteristics of the imaging member. This disadvantage is also present where the absorption of imaging energies and the generation of charge carriers is performed by one component of a binder layer (hereinafter functionally designated as the "charge carrier generating material") and the transport of charge carriers through the bulk of said layer by a second chemically distinct component (hereinafter referred to as "electronically active matrix material"), U.S. Pat. No. 3,121,007 and U.K. Pat. No. 1,343,671.

In order to avoid the cyling limitations often inherent in such single layered systems, it has been proposed that the functions of (a) charge carrier generation (resulting from photoactivation) and (b) charge carrier transport can be performed more satisfactorily—(with respect to cycling)—where each of these two separate functions is performed by contiguous but separate layers (U.K. Pat. No. 1,337,228 and Can. Pat. No. 932,199). In these multi-layered configurations, absorption of imaging energies and generation of charge carriers is exclusively limited to the layer of photogenerator materials. Substantial absorption and photogeneration of charge carriers within the bulk of the charge carrier transport layer can reportedly impair the cycling characteristics of this type of composite and thus is to be avoided. In U.K. Pat. No. 1,337,228, the transport layer is capable of facile transport of either holes or electrons which are injected into it from the layer of light-absorbing charge carrier generating materials contiguous therewith. In Can. Pat. No. 932,199 the charge carrier transport layer is capable of facile transport of electrons injected into it from a contiguous layer of light-absorbing charge carrier generating material. Neither patent specifically discloses a polymer having an electron acceptor moiety capable of satisfactory performance in such a transport layer. The Canadian patent does indicate that such polymers can be expected to perform in a manner equivalent to binder layers containing electron acceptor material.

Monomers having relatively weak electron acceptor groups pendant therefrom are disclosed in U.S. Pat. No. 3,418,116 and U.S. Pat. No. 3,697,264. In each instance these monomers are copolymerized with a second monomer having pendant therefrom an electron donor group. The resulting polymers reportedly are photoconductive due to the charge transfer interaction between adjacent moieties of differing electron affinities.

Attempts to prepare monomers having relatively strong electron acceptor groups (groups having an electron affinity in excess of about 0.7 electron volts) have been generally unsuccessful. This fact is borne out by the relatively few disclosures of strong electron acceptor functional monomers reported in the technical literature.

Ordinarily, the preparation of copolymers having strong electron acceptor groups appended from their backbone is beset with a number of difficulties. Due to the strong electron affinity of such pendant groups, it is virtually impossible to initiate polymerization of such monomers by free-radical techniques, since the electron acceptor moiety quenches the free radical prior to substantial polymerization of the monomer. This problem has led to attempts at introducing electron withdrawing substituents on groups pendant from a preformed polymer which does not already inherently possess strong electron acceptor properties. This technique also encounters serious synthesis hurdles since attempts at, for example, nitration of poly(vinylfluorenone) results in degradation of the polymer and reduction in its solubility in common solvents (presumably due to crosslinking).

In both U.K. Pat. No. 1,337,228 and Can. Pat. No. 932,199 discussed previously, it was indicated that electron acceptor systems can be prepared by dispersing and/or dissolving a nonpolymeric electron acceptor in a suitable binder and casting or coating this composition as a film on a layer of charge carrier generating materials. In terms of long term cycling stability, such binder system transport layers are not equivalent to transport layers prepared from polymers. Such binder layers can at best be described as metastable, undergoing a progressive decline in their electronic properties. Such instability is believed to be due in part to the tendency of such nonpolymeric materials to migrate within the polymeric binder and thereby cause phase separation due to crystallization. Thus, such binder layer transport layers would be precluded from use in a composite photoconductive layer requiring repeated cycling of this imaging member over an extended period of time, since the electronic properties of the imaging member would not be capable of remaining within the machine specifications for such a device. The electron transport layer configuration of the multi-layered photoconductor referred to in the above patents is superior to the hole transport layer system in that the electron transport system is relatively insensitive to oxidative degradation and unlike the hole transport analog, is capable of maintaining more stable electronic performance, thus, prolonging its useful lifetime within an electrophotographic reproduction system.

Accordingly, it is the object of this invention to remedy the above as well as related deficiencies in the prior art.

More specifically, it is the object of this invention to provide a process for preparation of monomers which can be readily polymerized to polymers having the capability for facile electron transport.

It is another object of this invention to provide a multi-layered photoconductive composite wherein charge carrier generation and charge carrier transport are preformed by separate but contiguous layers.

It is yet another object of this invention to employ such multi-layered photoconductive composite in an electrophotographic reproduction method.

SUMMARY OF THE INVENTION

The above and related objects are achieved by providing a process for preparation of monomers of the following formula:

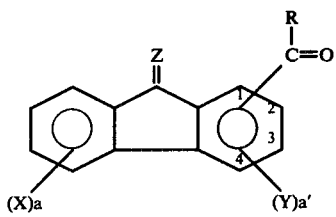

wherein
R is

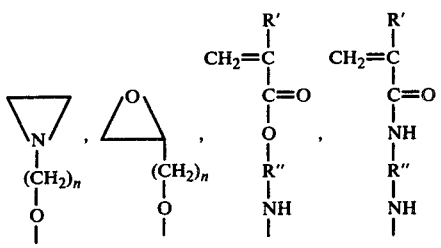

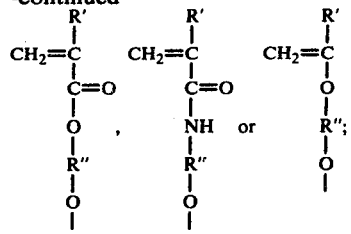

R' is hydrogen or methyl;
R'' is alkyl of 1–10 carbon atoms;
X and Y are independently selected from the group consisting of $NO_2$, halogen, cyano and $-CF_3$;
Z is oxygen or dicyanomethylene;
a and a' can range from 0–3; and
n is 1–10.

These monomers can be readily polymerized to polymers suitable for use in electrophotographic imaging members and methods. These monomers are prepared by the esterification of an acid chloride derivative of fluorenone or an acid chloride derivative of a substituted fluorenone with a hydroxyl or amino functional monomer reactant in the presence of a tertiary amine. The polymeric product of this esterification reaction can be polymerized in the same manner as the monomer reactant used in its preparation.

DESCRIPTION OF THE INVENTION INCLUDING PREFERRED EMBODIMENTS

The starting materials used in preparation of the monomers of this invention can be prepared by techniques and with equipment disclosed in the technical literature. In a number of instances, the starting materials used in such synthesis are also commercially available.

The fluorenone reactant used in preparation of the monomers of this invention can be initially prepared by at least three different techniques (depending upon the position of attachment of the carboxylic acid substituents to the fluorenone ring). Fluorenone-1-carboxylic acid can be prepared by reaction of fluoranthrene with chromic acid in acetic acid, J. Am. Chem. Soc. 57, 2174 (1935). Fluorenone-2-carboxylic acid can be prepared by reaction of fluorene with acetic acid anhydride in the presence of a Lewis acid followed by exposure to a strong oxidizing agent in order to convert it to the corresponding fluorenone, J. Org. Chem. 35, 2762 (1970). Fluorenone-4-carboxylic acid can be prepared by reaction of diphenic acid with sulphuric acid under the appropriate conditions, Fieser and Fieser "Advanced Organic Chemistry" Rheinhold Publishing Corporation, page 807 (1961). Each of the above carboxylic acid derivatives of fluorenone can be converted to the corresponding nitro analog by standard nitration techniques. The carboxylic acid derivative of fluorenone and the carboxylic acid derivative of nitrofluorenones can thereafter be readily converted to the corresponding acid chloride by reaction with thionyl chloride, phosphorous trichloride or phosphorous pentachloride.

The alcohol amino functional monomer reactants suitable for use in preparation of the monomers of this invention can be prepared by techniques and with equipment disclosed in the literature. In addition, many of these materials can be obtained from Polysciences Inc. of Warrington, Pa. Representative of alcohol and amino functional reactants which are suitable for use in preparation of such monomers include glycidol, 2-hydroxyethyl-methacrylate, 4-hydroxybutyl-methacrylate, 2-aminoethyl-methacrylate, 2-aminoethyl-methacrylamide, 2-hydroxyethyl-methacrylate, 2-hydroxyethyl-methacrylamide, vinyl-4-hydroxybutyl ether and N(2-hydroxyethyl) azirdine.

The monomers of this invention are prepared by simply contacting the acid chloride derivative of fluorenone or the acid chloride derivative of the substituted fluorenone and the alcohol or amino functional monomer in the presence of an appropriate amine in a suitable solvent. Acid which is liberated upon the esterification of these materials is absorbed by the amine. Amines which are suitable for use in this reaction mass include any of the tertiary amines, preferably the alkyl substituted tertiary amines. The solvent which provides the reaction medium for this esterification reaction can include any aprotic solvent within which the reactants are soluble. After the reaction has proceeded for the period desired, the ester produced during this interval is separated from the reaction mass by initial evaporation of the reaction medium followed by extraction of by-products of the esterification reaction and unreacted materials with the appropriate solvents.

Once having isolated the ester, it can be polymerized by conventional techniques. Where the monomer is the product of the esterification of a fluorenone carboxylic acid chloride with 2-hydroxyethyl methacrylate, this ester can be polymerized by standard free radical techniques. Alternatively, where the monomer is the product of the esterification of a fluorenone carboxylic acid chloride with glycidol, polymerization is achieved by the use of a standard ring opening catalyst such as boron trifluoride etherate and dialkyl zinc.

In addition to formation of homopolymers from these monomers, these monomers can also be copolymerized with other addition monomers. Such other addition monomers can contain pendant groups capable of charge transfer interaction with the pendant fluorenyl and substituted fluorenyl groups of these monomers. Polymeric compositions prepared from these monomers can also serve as binders or electronically active matrices for use in conjunction with other photoconductive materials.

The monomers, homopolymers and copolymers described hereinabove can be used alone or in combination with one another or in combination with other monomers and/or polymers in electrophotographic imaging members and methods. For example, the electronically active monomers of this invention can be dissolved/dispersed in a polymeric binder and films prepared therefrom. The polymeric binder can itself be electronically active or electronically inert. In the case where these monomers are used in conjunction with an active binder, such as poly(N-vinylcarbazole), charge transfer interaction will occur thereby forming a photoconductive composition having substantial spectral response in the visible region of the electromagnetic spectrum. These electronically active monomers are appreciably more soluble in both electronically active and electronically inert binders than, for example, 2,4,7-trinitro-9-fluorenone and, thus, higher loadings of such monomers can be used in conjunction with such binders without occasioning phase separation of the materials of the compositions.

Polymers and copolymers prepared from the above monomers can be formed into tough, flexible, chemically stable films by routine techniques with conventional equipment. The homopolymers prepared from the above monomers are only slightly photosensitive in the visible region of the electromagnetic spectrum and, therefore, are highly suitable for use as charge carrier transport layers in composite photoconductive insulating layers of the type disclosed in Can. Pat. No. 932,199. This composite photoconductor consists essentially of a layer of photoconductive material capable of substantial spectral response in the visible region of the electromagnetic spectrum and contiguous therewith an insulating layer of charge transport material incapable of substantial spectral response in the visible region of the electromagnetic spectrum. Upon photoactivation of this composite, charge carriers are generated in the photoconductive layer and injected into the charge carrier transport layer. The materials selected for these respective layers must be sufficiently closely matched electronically so as to permit the injection of carriers from one layer into the other. Where the polymeric materials prepared from the monomers of this invention are used in the transport layer, the resulting transport layer will be capable of facile transport of electrons. Photoconductive pigments, which can be used in the photoconductive layer, that is associated with transport layers prepared from the polymers derived from the monomer of this invention, include inorganic crystalline photoconductors such as cadmium sulfide, cadmium sulfoselenide, cadmium selenide, zinc sulfide, zinc oxide, trigonal selenium, and mixtures thereof. Typical inorganic photoconductive glasses which can be used in this photogenerative layer are amorphous selenium and its alloys (especially alloys of arsenic and tellurium). Representative of the organic photoconductors which can be used in such a photogenerator layer include phthalocyanine pigments and the photoinjecting pigments of benzimidazole, perylene, quinacridone, indigoid and polynuclear quinones.

In a typical composite photoconductive layer of the type referred to hereinabove, the photoconductive layer can range in thickness from about 0.02 to about 20 microns and the charge carrier transport layer a thickness in the range of from about 5 to about 100 microns; the ratio of thickness of the photogenerator layer to the transport layer being in the range of from about 1:2 to about 1:200.

The polymers prepared from the monomers of this invention are also suitable as electronically active binders for photoconductive pigments. In addition, the polymers of this invention can be sensitized by combining them with dyestuffs and/or electron donors (relative to the electron withdrawing substituent of the polymer) e.g. Lewis bases. These electron donors can be monomeric or polymeric. Upon combination of the polymers of this invention with Lewis bases, charge transfer interaction will occur thereby forming a highly colored charge transfer complex which is photoresponsive to light throughout a substantial portion of the visible band of the electromagnetic spectrum. This photoconductive composition can be used alone or in combination with other materials in electrophotographic imaging members and methods.

Where these monomers are copolymerized with other monomers, the electronic properties of the copolymer will differ from the properties of the homopolymer. In the event that these monomers are copolymerized with a comonomer devoid of carbocyclic or heterocyclic constituents, the resultant copolymer will generally be less electronically active than the homopolymer prepared from this same monomer. Where the comonomer does contain a carbocyclic and/or heterocyclic constituent, the electronically active constituent of the monomers of this invention can be expected to undergo some charge transfer interaction with the carbocyclic and/or heterocyclic constituent on the adjacent structural unit of the copolymer backbone (hereinafter referred to as "intrachain" charge transfer complexes) or with the carbocyclic and/or heterocyclic constituent on adjacent copolymer backbones (hereinafter referred to as "intrachain" charge transfer complexes). The presence of such carbocyclic and/or heterocyclic constituents can also be expected to increase the mobility of holes generated upon photoexcitation of the copolymer and/or holes which are injected into the copolymers from another source of charge carriers. These charge transfer copolymers will thus exhibit ambipolarity and can be used as a matrix for other photoconductive pigments and dyes without appreciable trapping of either species of charge carrier by the matrix. Of course, the ambipolar character of such a system presumes that the photoconductive pigment and dyes which are dispersed within the copolymers do not themselves appreciably trap either species of charge carrier.

The Examples which follow further define, describe and illustrate the preparation and use of the monomers and polymers of this invention. Apparatus and techniques used in preparation and evaluation of these materials are standard or as hereinbefore described. Parts and percentages appearing in such examples are by weight unless otherwise stipulated.

EXAMPLE I

Preparation of glycidyl-4,5,7-trinitro-9-fluorenone-2-carboxylate

Fluorene is initially reacted with acetic anhydride in the presence of aluminum chloride thereby forming 2-acetyl fluorene, as per J. Org. Chem. 35: 8 2765 (1970). 2-Acetyl fluorene is thereafter oxidized to fluorenone-2-carboxylic acid in the following manner (as per Organic Synthesis, Coll. Vol. III, p. 240). A 5 liter 3-necked round bottom flask, equipped with a magnetic stirring bar, reflux condenser and addition funnel is charged with 50 grams of 2-acetyl fluorene and 650 milliliters of glacial acetic acid. This solution is warmed sufficiently until the 2-acetyl fluorene is dissolved in the glacial acetic acid. A total of about 450 grams sodium dichromate dihydrate is slowly added to the solution over a period of about 60 minutes. After such addition is complete, the mixture is heated to boiling under reflux and 200 milliliters of acetic anhydride introduced into the reaction vessel through the addition funnel over a period of about 90 minutes. Heating under reflux conditions is continued overnight. The following morning, the hot solution is poured into 9 liters of hot water, stirred for 50 minutes and then filtered through a Buckner funnel. The filter cake is washed with four 400 milliliter portions of 2 percent sulfuric acid. The yellow product remaining in the funnel is thereafter transferred to a 4 liter beaker containing 700 milliliters of 5 percent potassium hydroxide. This mixture is stirred and heated for about 20 minutes on a steam bath. When the temperature of the mixture reaches 70° C., it is filtered. The insoluble material is subsequently treated with several 50 milliliter portions of hot 5 percent potassium hydroxide. The filtrates are collected and combined, treated with a few grams of activated charcoal and filtered. The filtered solution is then heated to a temperature in the range of from between 65° to 70° C. with vigorous agitation and 200 milliliters of 18 percent hydrochloric acid added by dropwise addition. A thick yellow voluminous precipitate is formed which is heated for an additional 15 minutes at 85° C. After filtration, the product is again washed with five 200 milliliter portions of hot water and air dried overnight. Further drying is accomplished by vacuum treatment at 100° C. for 16 hours. Yield 25.1 grams bright yellow crystals of fluorenone-2-carboxylic acid.

The fluorenone-2-carboxylic acid is thereafter nitrated in the conventional manner with a mixture of fuming nitric acid and concentrated sulfuric acid. The nitrated product is recovered and purified in the conventional manner. Analysis of this product indicates it to be 4,5,7-trinitro-9-fluorenone-2-carboxylic acid. This product is subsequently contacted with thionyl chloride thereby producing 4,5,7-trinitro-9-fluorenone-2-carboxylic acid chloride.

Into a 250 milliliter Erlenmeyer flask are placed 10.03 grams (0.026 moles) of 4,5,7-trinitro-9-fluorenone-2-carboxylic acid chloride and 100 milliliters of tetrahydrofuran. This mixture is stirred by means of a magnetic stirring bar until the above materials are completely dissolved in the solvent. About 2.60 grams (0.026 moles) of triethylamine are dissolved in 20 milliliters of tetrahydrofuran and slowly added to the contents of the flask. Upon completion of this addition, some cloudiness of the solution is noted. To the solution is subsequently added 2.1 grams (0.029 moles) of glycidol dissolved in 200 milliliters of tetrahydrofuran. The addition of the glycidol solution to the Erlenmeyer flask is accomplished by dropwise addition. Subsequent to such addition, some precipitate is observed in the flask. The materials in the flask are allowed to react for 90 minutes. This previously noted precipitate, subsequently identified as triethylamine hydrochloride, is removed from the flask by filtration and the solution which is recovered carefully evaporated to dryness at 35° C. on a rotary evaporator. The solids which remain are taken up in methylene chloride and extracted with water for removal of residual traces of triethylamine hydrochloride. The hydrated product is extracted with several portions of methylene chloride. The methylene chloride solution of the monomer is dried over magnesium sulfate, filtered and evaporated to dryness on a rotary evaporator. The foam-like solid which forms is taken up in 10 milliliters methylene chloride per gram of solid and precipitated by stirring into hexane. A very light yellow powdery material is obtained which is subsequently identified by standard chemical analysis as glycidyl-4,5,7-trinitro-9-fluorenone-carboxylate. The synthesis yield is approximately 70 percent.

EXAMPLE II

Preparation of 2-ethylmethacryl-4,5,7-trinitro-9-fluorenone-2-carboxylate

This material is prepared according to the procedures described in Example I merely by substitution of 2-hydroxyethyl methacrylate for glycidol.

EXAMPLE III

Preparation of 2-ethylmethacrylamide-4,5,7-trinitro-9-fluorenone-2-carboxylate

This material is prepared according to the procedures described in Example I merely by substitution of 2-hydroxyethyl methacrylamide for glycidol.

EXAMPLE IV

Preparation of 2-aminoethylmethacryl-4,5,7-trinitro-9-fluorenone-2-carboxylate

This material is prepared according to the procedures described in Example I merely by substitution of 2-aminoethyl methacrylate for glycidol.

EXAMPLE V

Preparation of 2-aminoethylmethacrylamide-4,5,7-trinitro-9-fluorenone-2-carboxylate This material is prepared according to the procedures described in Example I merely by substitution of 2-aminoethylmethacrylamide for glycidol.

EXAMPLE VI

Preparation of N-(2-butyl) azirdine-4,5,7-trinitro-9-fluorenone-2-carboxylate

This material is prepared according to the procedures described in Example I merely by substitution of N(2-hydroxybutyl) azirdine for glycidol.

EXAMPLE VII

Preparation of vinyl-(4-butyl) ether-4,5,7-trinitro-9-fluorenone-2-carboxylate

This material is prepared according to the procedures described in Example I merely by substitution of vinyl-4-hydroxybutyl ether for glycidol.

EXAMPLE VIII

Polymerization of glycidyl-4,5,7-trinitro-9-fluorenone-2-carboxylate

A 100 milliliter three-necked round bottom flask equipped with a magnetic stirrer is charged with 1.0 grams glycidyl-4,5,7-trinitro-9-fluorenone-2-carboxylate and 20 milliliters methylene chloride (which has been previously purified by passage through an alumina column). Upon intermixing of these two materials a deep brownish-red solution is formed. The initiator for this polymerization is prepared by diluting 1 milliliter boron trifluoride etherate to 10 milliliters with methylene dichloride. Both the reaction vessel and its contents and the initiator are now chilled to 0° C. The reaction vessel is purged of air with nitrogen and 1 weight percent (0.1 milliliter) of the initiator introduced into the reaction vessel via a syringe which has been inserted through a rubber septom of the reaction vessel. Immediately after introduction of the initiator, the contents of the flask become cloudy followed by a general lightening in color of the solution. During the course of the next two hours, a precipitate is formed in the flask. The contents of flask is thereafter emptied into a beaker containing 100 milliliters of methanol and precipitate, which is formed, separate from the methanol by filtration. This precipitate is purfied by recrystallization from THF with methanol. Yield 0.17 grams polymer, $M\bar{n}$ = 2,200 (as determined by standard vapor pressure osmometry techniques).

EXAMPLE IX

Polymerization of 2'-ethylmethacryl-4,5,7-trinitro-9-fluorenone-2-carboxylate

Into a polymer tube is added 2.5 grams of the monomer obtained from Example II, 8 milliliters acetone (which has been previously dried over a 3 Angstrom unit molecular sieve) and 0.025 grams azobisisobutylnitrile (0.1 weight percent). The polymer tube and its contents are then subjected to 2 freeze-thaw cycles before sealing under a vacuum. The sealed polymer tube and its contents are placed in a water bath at 60° C. and the polymerization allowed to proceed for 17 hours. No noticeable color or viscosity change is apparent at the end of this interval. The contents of the tube are then emptied into methanol for precipitation of the polymeric product. Yield 0.38 grams of orange color polymer, $M\bar{n}$ = 3,520 (as determined by standard vapor pressure osmometry techniques).

EXAMPLE X

A tetrahydrofuran solution containing 25 weight percent of the polymer of Example VIII is draw bar coated on a thin layer (approximately 0.5 microns) of amorphous selenium which has been previously vacuumed coated on a ball-grained aluminum plate. The amount of polymer transferred to the selenium plate is sufficient to form a layer having a dry film thickness of approximately 12 microns. Upon substantially complete evaporation of solvent residues from this polymer layer, the electrophotographic properties of the photoconductive composite are evaluated. Such evaluation consist essentially of charging the surface of the polymer coating to a positive potential of about 800 volts followed by imagewise exposure to activating electromagnetic radiation. The latent image formed on the surface of the polymer layer is developed with negatively charged toner particles and the toner image thereafter transferred to a sheet of plain paper. The toner residues remaining on the surface of the polymer coating are removed by wiping with a soft cotton cloth and the reproduction cycle repeated. Copy quality is good and is reproducible.

EXAMPLE XI

A 25 weight percent tetrahydrofuran solution containing equal parts of the monomer of Example I and polyethylene terephthlate resin (Mylar 49000, available from E. I. du Pont de Nemours & Company) is draw bar coated over a thin layer (approximately 0.5 microns) of amorphous selenium, which has been previously vacuum coated on a ball-grained aluminum plate. The amount of solids overcoated on the selenium plate is sufficient to form a layer having a dry film thickness of approximately 12 microns. Upon substantially complete evaporation of the solvent residues from this overcoating, the electrophotographic performance of the plate is evaluated in the same manner described in Example X. Copy quality is satisfactory and reproducible.

EXAMPLE XII

The procedure of Example X is repeated except for substitution of the polymer of Example IX for the polymer of Example VIII. Electrophotographic evaluation

EXAMPLE XIII

The procedures of Example XI is repeated with the monomer of Examples II–VII respectively. Electrophotographic performance is comparable to the achievable in Example XI.

EXAMPLE XIV

About 2 grams of the polymer of Example VIII and 2 grams N-ethylcarbazole are dissolved in 25 milliliters of tetrahydrofuran and the resulting solution draw bar coated on an aluminized plastic film (aluminized Mylar, available from E. I. duPont de Nemours & Company). The amount of solids transferred to the aluminum surface of the plastic film is sufficient to form a dry film having a thickness of approximately 20 microns. Due to the charge transfer interaction between the electron acceptor groups of the polymer and the N-ethylcarbazole, the polymeric coating is highly colored. After the polymer coating is substantially free of solvent residues, it is evaluated electrophotographically by initially charging its surface to a positive potential of about 800 volts followed by imagewise exposure to white light. The latent electrostatic image formed on its surface is thereafter developed with negatively charged toner particles and the toner image subsequently transferred to a sheet of plain paper. The surface of the polymeric coating is wiped with a cotton cloth for removal of toner residues and the reproduction cycle repeated. Copy quality is acceptable and reproducible.

What is claimed is:

1. Homopolymers comprising the product of the addition polymerization of a monomer represented by the structural formula

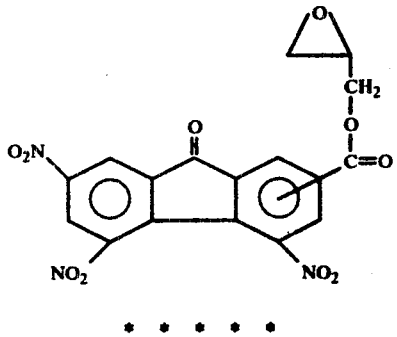

* * * * *